(12) United States Patent
Bacigalupi

(10) Patent No.: US 9,585,924 B1
(45) Date of Patent: Mar. 7, 2017

(54) HERBAL WATER BEVERAGE

(71) Applicant: Anthony Steven Bacigalupi, San Leandro, CA (US)

(72) Inventor: Anthony Steven Bacigalupi, San Leandro, CA (US)

(73) Assignee: Hemp2O LLC, San Leandro, CA (US)

(*) Notice: Subject to any disclaimer, the term of this patent is extended or adjusted under 35 U.S.C. 154(b) by 0 days.

(21) Appl. No.: 14/863,741

(22) Filed: Sep. 24, 2015

Related U.S. Application Data

(60) Provisional application No. 62/054,716, filed on Sep. 24, 2014.

(51) Int. Cl.

| | |
|---|---|
| *A01N 65/00* | (2009.01) |
| *A61K 36/185* | (2006.01) |
| *A61K 9/107* | (2006.01) |
| *A61K 9/00* | (2006.01) |
| *A61K 47/46* | (2006.01) |
| *A61K 47/26* | (2006.01) |
| *A23L 2/38* | (2006.01) |
| *A23L 2/52* | (2006.01) |
| *A23L 2/60* | (2006.01) |

(52) U.S. Cl.
CPC ............. *A61K 36/185* (2013.01); *A23L 2/38* (2013.01); *A23L 2/52* (2013.01); *A23L 2/60* (2013.01); *A61K 9/0095* (2013.01); *A61K 9/107* (2013.01); *A61K 47/26* (2013.01); *A61K 47/46* (2013.01); *A23V 2002/00* (2013.01)

(58) Field of Classification Search
CPC ...................................................... A61K 36/00
USPC ............................................................ 424/725
See application file for complete search history.

(56) References Cited

U.S. PATENT DOCUMENTS

2016/0213041 A1* 7/2016 Johns .................... A23C 9/1526

* cited by examiner

*Primary Examiner* — Michael Meller
(74) *Attorney, Agent, or Firm* — Larry D. Johnson

(57) ABSTRACT

An herbal water beverage containing hemp preferably includes water, sugar, organic flavoring, vitamins, and hemp oil. Organic hemp seed oil is added to a water based solution of organic gum arabic and organic maltodextrin. The solution is homogenized and then spray dried. During the drying process the hemp seed oil is surrounded by a matrix of maltodextrin and gum arabic that protects it from exposure to air (oxidation). The water is removed in a dryer through evaporation leaving hemp oil droplets surrounded by a film of gum arabic and maltodextrin matrix. The gum arabic acts as an emulsifier, retarding the separation of the hemp seed oil once it is added to the water, sugar, organic flavoring, and vitamins to form the finished aqueous beverage.

1 Claim, No Drawings

HERBAL WATER BEVERAGE

CROSS REFERENCE TO RELATED APPLICATIONS

The present application claims the benefit of the filing date of U.S. Provisional Patent Application Ser. No. 62/054,716, filed Sep. 24, 2014. The foregoing application is incorporated by reference in its entirety as if fully set forth herein.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates generally to herbal waters, flavored waters, and vitamin waters, and more particularly to an improved herbal water beverage.

BACKGROUND INFORMATION AND DISCUSSION OF RELATED ART

Herbal waters, flavored waters, and vitamin waters are all well known, but many do not provide desired benefits. Notably, most lack Omega 3's and natural anti-oxidants from a natural source.

The foregoing information reflects the current state of the art of which the present inventor is aware. Reference to, and discussion of, this information is intended to aid in discharging Applicant's acknowledged duty of candor in disclosing information that may be relevant to the examination of claims to the present invention. However, it is respectfully submitted that none of the above information discloses, teaches, suggests, shows, or otherwise renders obvious, either singly or when considered in combination, the invention described and claimed herein.

SUMMARY OF THE INVENTION

The present invention provides an improved herbal water beverage in the form of an herbal water beverage containing hemp. The inventive beverage preferably includes water, sugar, organic flavoring, vitamins, and hemp oil. In the preferred embodiment, organic hemp seed oil is added to a water based solution of organic gum arabic and organic maltodextrin. The solution is homogenized and then spray dried. During the drying process the hemp seed oil is surrounded by a matrix of maltodextrin and gum arabic that protects it from exposure to air (oxidation). The water is removed in a dryer through evaporation leaving hemp oil droplets surrounded by a film of gum arabic and maltodextrin matrix. The gum arabic acts as an emulsifier, retarding the separation of the hemp seed oil once it is added to the water, sugar, organic flavoring, and vitamins to form the finished aqueous beverage.

The inventive herbal water beverage may be produced in a variety of flavors, e.g., Grape, Orange, Strawberry, Passion Fruit, and Raspberry Lime. The beverage provides Omega 3's and has natural anti-oxidants from the hemp oil in the product. There are numerous beneficial factors associated with drinking the inventive beverage, for example, the nutritional properties; the Omega 3's; benefits provided for stress, blood pressure and cholesterol control; early signs indicate medicinal value related to epilepsy/seizure control; and the potential for cancer prevention and treatment.

It is therefore an object of the present invention to provide a new and improved herb infused water.

It is another object of the present invention to provide a new and improved herb infused flavored water.

A further object or feature of the present invention is a new and improved herb infused vitamin water.

Other novel features which are characteristic of the invention, as to organization and method of operation, together with further objects and advantages thereof will be better understood from the following description. The various features of novelty which characterize the invention are pointed out with particularity in the claims annexed to and forming part of this disclosure. The invention resides not in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of this application, which is measured by the claims, nor is it intended to be limiting as to the scope of the invention in any way.

Certain terminology and derivations thereof may be used in the following description for convenience in reference only, and will not be limiting. For example, references in the singular tense include the plural, and vice versa, unless otherwise noted.

DETAILED DESCRIPTION OF THE INVENTION

The present invention provides an improved herbal water beverage in the form of a flavored herbal water beverage containing hemp. The inventive beverage preferably includes water, a sweetening agent such as sugar, flavoring, vitamins, and hemp oil. All of the ingredients are preferably organic when applicable.

The hemp oil in the inventive beverage needs to be water soluble in order to avoid separation. In the preferred embodiment, organic hemp seed oil is added to a water based solution of gum arabic (preferably organic) and maltodextrin (preferably organic). The solution is homogenized and then spray dried. During the drying process the hemp seed oil is surrounded by a matrix of maltodextrin and gum arabic that protects it from exposure to air (oxidation). The water is removed in a dryer through evaporation leaving hemp oil droplets surrounded by a film of gum arabic and maltodextrin matrix. The gum arabic acts as an emulsifier, retarding the separation of the hemp seed oil once it is added to the water, sugar, organic flavoring, and vitamins to form the finished aqueous beverage.

Accordingly, the invention may be characterized as an herbal water beverage comprising water, a sweetening agent, flavoring, and hemp oil droplets surrounded by a film of gum arabic and maltodextrin matrix to retard separation of the hemp oil.

The invention may also be characterized as a method of manufacturing an herbal water beverage comprising adding hemp seed oil to a water based solution of gum arabic and maltodextrin; homogenizing the solution; drying the solution to produce hemp oil droplets surrounded by a matrix of maltodextrin and gum arabic; and adding the hemp oil droplets to water, a sweetening agent, and flavoring to form the finished beverage.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A method of manufacturing an herbal water beverage consisting essentially of:
    adding hemp seed oil to a water based solution of gum arabic and maltodextrin to form a solution;
    homogenizing the solution;
    drying the solution to produce hemp oil droplets surrounded by a matrix of maltodextrin and gum arabic; and
    adding the hemp oil droplets to water to produce said herbal water beverage.

* * * * *